(12) United States Patent
Hammon et al.

(10) Patent No.: US 9,958,201 B2
(45) Date of Patent: May 1, 2018

(54) COLUMN FOR THERMAL TREATMENT OF A FLUID

(71) Applicant: BASF SE, Ludwigshafen (DE)

(72) Inventors: Ulrich Hammon, Mannheim (DE); Thomas Walter, Hassloch (DE)

(73) Assignee: BASF SE, Ludwigshafen (DE)

( * ) Notice: Subject to any disclaimer, the term of this patent is extended or adjusted under 35 U.S.C. 154(b) by 199 days.

(21) Appl. No.: 14/817,351

(22) Filed: Aug. 4, 2015

(65) Prior Publication Data

US 2016/0040929 A1 Feb. 11, 2016

Related U.S. Application Data

(60) Provisional application No. 62/033,157, filed on Aug. 5, 2014.

(30) Foreign Application Priority Data

Aug. 5, 2014 (DE) ........................ 10 2014 215 437

(51) Int. Cl.
*F25J 3/02* (2006.01)
*C07C 67/54* (2006.01)
(Continued)

(52) U.S. Cl.
CPC .............. *F25J 3/0271* (2013.01); *B01D 3/20* (2013.01); *B01D 3/22* (2013.01); *B01D 3/32* (2013.01);
(Continued)

(58) Field of Classification Search
CPC ... B01D 3/20; B01D 3/22; B01D 3/32; B01D 3/4261; C07C 45/783; C07C 45/80; C07C 51/48; F25J 3/0271
(Continued)

(56) References Cited

U.S. PATENT DOCUMENTS 3,932,500 A * 1/1976 Duembgen ........... C07C 51/252
203/63
3,988,213 A 10/1976 Yoshida et al.
(Continued)

FOREIGN PATENT DOCUMENTS

DE 216 633 A1 12/1984
DE 279 822 A1 6/1990
(Continued)

*Primary Examiner* — Charles Bushey
(74) *Attorney, Agent, or Firm* — Oblon, McClelland, Maier & Neustadt, L.L.P.

(57) ABSTRACT

The present disclosure includes a column (1) having a cylindrical, vertical column body (2) forming a column cavity (3), and a mass transfer tray (4) disposed in the column cavity (3) and forming a collecting area (5). The column (1) is characterized by a circulation device (9) having at least one drain orifice (10) formed in the column body (2) above the collecting area (5), a circulation line (11) in fluid connection with the drain orifice (10) and at least one recycling orifice (14; 14-1 to 14-3) which is in fluid connection with the circulation line (11) and is formed in the column body (2) above the collecting area (5). Also disclosed herein is a thermal separating process in which a gas ascends within a column (1) of the present disclosure, and a liquid descends within the column (1), said gas and/or liquid containing (meth)acrylic monomers.

18 Claims, 4 Drawing Sheets

Figure 1:
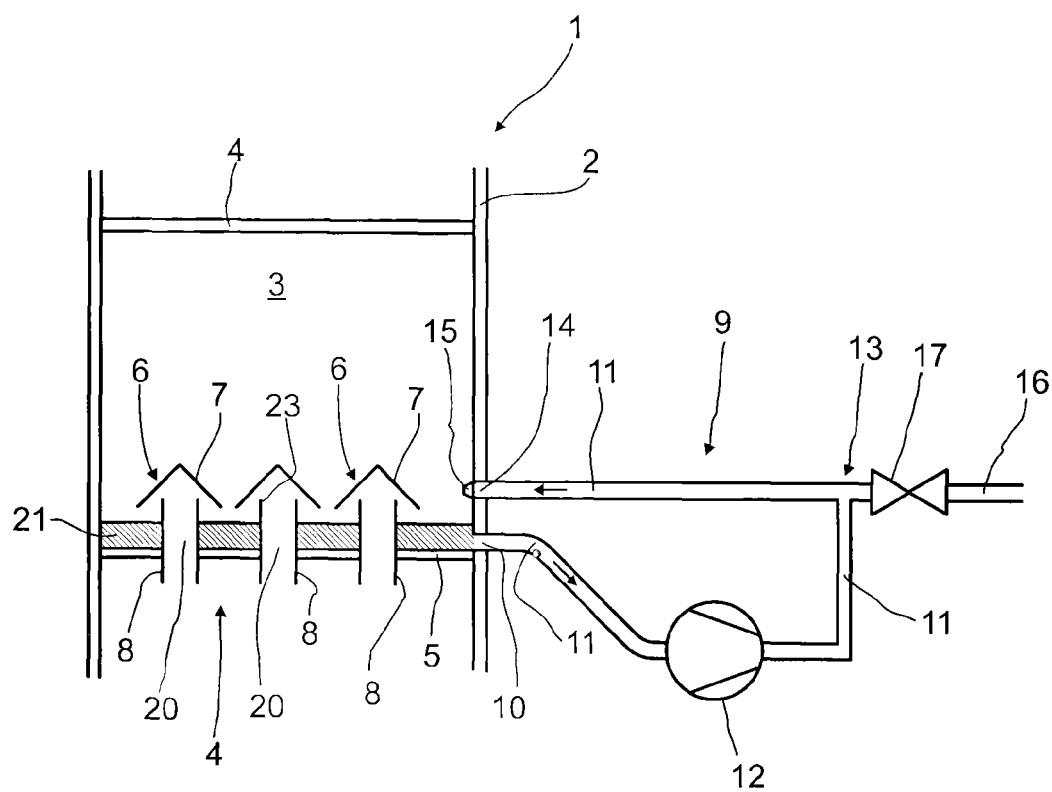

(51) Int. Cl.
*C07C 45/82* (2006.01)
*B01D 3/20* (2006.01)
*B01D 3/42* (2006.01)
*C07C 45/78* (2006.01)
*C07C 45/80* (2006.01)
*C07C 51/44* (2006.01)
*C07C 51/48* (2006.01)
*B01D 3/22* (2006.01)
*B01D 3/32* (2006.01)

(52) U.S. Cl.
CPC .......... *B01D 3/4261* (2013.01); *C07C 45/783* (2013.01); *C07C 45/80* (2013.01); *C07C 45/82* (2013.01); *C07C 51/44* (2013.01); *C07C 51/48* (2013.01); *C07C 67/54* (2013.01)

(58) Field of Classification Search
USPC ................................. 261/114.1, 114.2, 114.5
See application file for complete search history.

(56) References Cited

U.S. PATENT DOCUMENTS

| | | | | |
|---|---|---|---|---|
| 4,247,368 A * | 1/1981 | Bannon | ............... | B01D 3/14 202/158 |
| 6,679,939 B1 * | 1/2004 | Thiel | ............... | B01D 3/14 202/158 |
| 7,622,607 B2 * | 11/2009 | Fauconet | ............... | C07C 51/42 562/600 |
| 8,093,437 B2 * | 1/2012 | Fukuoka | ............... | B01D 3/009 202/152 |
| 2009/0288939 A1 * | 11/2009 | Smith | ............... | B01D 3/14 202/158 |
| 2011/0308931 A1 * | 12/2011 | Tamminen | ............... | B01D 3/06 203/88 |
| 2013/0267751 A1 * | 10/2013 | Favilli | ............... | B01D 1/28 585/806 |

FOREIGN PATENT DOCUMENTS

| | | |
|---|---|---|
| DE | 197 40 252 A1 | 3/1999 |
| DE | 197 40 253 A1 | 3/1999 |
| DE | 199 24 532 A1 | 11/2000 |
| DE | 199 24 533 A1 | 11/2000 |
| DE | 101 56 988 A1 | 5/2003 |
| DE | 101 59 823 A1 | 6/2003 |
| DE | 102 18 419 A1 | 6/2003 |
| DE | 102 57 915 A1 | 10/2003 |
| DE | 102 30 219 A1 | 1/2004 |
| DE | 103 36 386 A1 | 3/2004 |
| DE | 102 43 625 A1 | 4/2004 |
| DE | 103 32 758 A1 | 5/2004 |
| DE | 10 2010 001 228 A1 | 2/2011 |
| EP | 0 700 714 A1 | 3/1996 |
| EP | 0 700 893 A1 | 3/1996 |
| EP | 0 882 481 A1 | 12/1998 |
| EP | 0 982 287 A1 | 3/2000 |
| EP | 0 982 289 A2 | 3/2000 |
| EP | 1 029 573 A2 | 8/2000 |
| EP | 1 125 912 A2 | 8/2001 |
| EP | 1 279 429 A1 | 1/2003 |
| EP | 1 704 906 A1 | 9/2006 |
| WO | WO 2004/035514 A1 | 4/2004 |
| WO | WO 2008/090190 A1 | 7/2008 |

* cited by examiner

COLUMN FOR THERMAL TREATMENT OF A FLUID

This application is based upon and claims the benefit of priority to U.S. Provisional Application No. 62/033,157, which was filed on Aug. 5, 2014, and also claims the benefit of priority to German Application No. 10 2014 215 437.5, which was filed on Aug. 5, 2014.

The present invention relates to a column for thermal treatment of a fluid. The column has a cylindrical, vertical column body which forms a column cavity, and a mass transfer tray which is arranged in the column cavity and forms a collecting area. The column is especially a separating column. The invention further relates to a thermal separation process between at least one gas ascending within a column and at least one liquid descending within the column.

In separating columns, gaseous (ascending) and liquid (descending) streams are in many cases conducted in countercurrent, at least one of the streams especially comprising a (meth)acrylic monomer. As a result of the inequilibria that exist between the streams, heat and mass transfer takes place, which ultimately causes the removal (or separation) desired in the separating column. In this document, such separating processes shall be referred to as thermal separating processes.

Examples of, and hence elements of, the expression "thermal separating processes" used in this document are fractional condensation (cf., for example, DE 19924532 A1, DE 10243625 A1 and WO 2008/090190 A1) and rectification (in both cases, ascending vapor phase is conducted in countercurrent to descending liquid phase; the separating action is based on the vapor composition at equilibrium being different from the liquid composition), absorption (at least one ascending gas is conducted in countercurrent to at least one descending liquid; the separating action is based on the different solubility of the gas constituents in the liquid) and desorption (the reverse process of absorption; the gas dissolved in the liquid phase is removed by lowering the partial pressure; if the partial pressure of the material dissolved in the liquid phase is lowered at least partly by passing a carrier gas through the liquid phase, this thermal separating process is also referred to as stripping; alternatively or additionally (simultaneously as a combination), the lowering of the partial pressure can also be brought about by lowering the working pressure).

For example, the removal of (meth)acrylic acid and/or (meth)acrolein from the product gas mixture of the catalytic gas phase oxidation can be conducted in such a way that the (meth)acrylic acid and/or the (meth)acrolein is first subjected to basic removal by absorption into a solvent (e.g. water or an organic solvent) or by fractional condensation of the product gas mixture, and the absorbate or condensate obtained is subsequently separated further to obtain (meth) acrylic acid and/or (meth)acrolein of greater or lesser purity (cf., for example, DE-10332758 A1, DE 10243625 A1, WO 2008/090190 A1, DE 10336386 A1, DE 19924532 A1, DE 19924533 A1, DE 102010001228 A1, WO 2004/035514 A1, EP 1125912 A2, EP 982289 A2, EP 982287 A1 and DE 10218419 A1).

The notation "(meth)acrylic monomers" in this document is an abbreviated form of "acrylic monomers and/or methacrylic monomers".

The term "acrylic monomers" in this document is an abbreviated form of "acrolein, acrylic acid and/or esters of acrylic acid".

The term "methacrylic monomers" in this document is an abbreviated form of "methacrolein, methacrylic acid and/or esters of methacrylic acid".

In particular, the (meth)acrylic monomers addressed in this document shall comprise the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparation of polymers which find use, for example, as adhesives or as water-superabsorbing materials in hygiene articles.

On the industrial scale, (meth)acrolein and (meth)acrylic acid are prepared predominantly by catalytic gas phase oxidation of suitable $C_3/C_4$ precursor compounds (or of precursor compounds thereof). In the case of acrolein and acrylic acid, such precursor compounds used are preferably propene and propane. In the case of methacrylic acid and of methacrolein, isobutene and isobutane are preferred precursor compounds.

As well as propene, propane, isobutene and isobutane, however, suitable starting materials are also other compounds comprising 3 or 4 carbon atoms, for example isobutanol, n-propanol or precursor compounds thereof, for example the methyl ether of isobutanol. Acrylic acid can also be obtained by oxidation of acrolein under gas phase catalysis. Methacrylic acid can also be obtained by oxidation of methacrolein under gas phase catalysis.

In the context of such preparation processes, it is normal to obtain product gas mixtures from which the (meth)acrylic acid and/or the (meth)acrolein have to be removed.

Esters of (meth)acrylic acid are obtainable, for example, by direct reaction of (meth)acrylic acid and/or (meth)acrolein with the appropriate alcohols. However, in this case too, product mixtures are at first obtained, from which the (meth)acrylic esters have to be removed.

The separating columns in which these separating processes are conducted comprise separating internals. In the thermal separating processes, these have the purpose of increasing the surface area for the heat and mass transfer which brings about the separation in the separating column ("the transfer area").

Useful internals of this kind include, for example, structured packings, random packings and/or trays, which are also referred to as mass transfer trays. Frequently, separating columns used are those which comprise at least one sequence of mass transfer trays as a portion of the separating internals.

The purpose of mass transfer trays is to provide areas having essentially continuous liquid phases in the separating column in the form of liquid layers that form thereon. The surface of the vapor and/or gas stream which ascends within the liquid layer and is distributed in the liquid phase is then the crucial transfer area.

A sequence of mass transfer trays is understood to mean a sequence (a succession) of at least two mass transfer trays generally of the same design (i.e. identical), arranged one above another in the separating column. Advantageously for application purposes, the clear distance between two immediately successive mass transfer trays in such a series (sequence) of mass transfer trays is uniform (meaning that the mass transfer trays are arranged equidistantly one above another in the separating column).

The simplest embodiment of a mass transfer tray is called a trickle sieve tray. This comprises a plate, or plate segments joined to form a plate, having essentially planar passage orifices, for example round holes and/or slots, for the ascending gas or vapor phase (the terms "gaseous" and "vaporous" are used synonymously in this document) distributed over the plate (cf., for example, DE 10230219 A1, EP 1279429 A1, U.S. Pat. No. 3,988,213 and EP 1029573 A1). Any orifices beyond these (for example at least one downcomer (at least one drain segment)) are generally not present in trickle sieve trays. As a result of this absence of downcomers, both the gas ascending within the separating column (the vapor ascending within the separating column) and the liquid descending within the separating column have to move, flowing in opposite directions, alternating in time, through the (same) passage orifices (through the open cross sections of the passages). Reference is also made to the "dual flow" of ascending gas and descending liquid through the passage orifices, which is the reason why the literature frequently also uses the term "dual-flow trays" for mass transfer trays of this type.

The cross section of the passage orifices of a dual-flow tray is matched in a manner known per se to the load thereon. If the cross section is too small, the ascending gas passes through the passage orifices at such a high velocity that the liquid descending within the separating column is entrained essentially without separating action. If the cross section of the passage orifices is too great, ascending gas and descending liquid move past one another essentially without exchange, and the mass transfer tray is at risk of running dry.

In other words, the separation-active working range of a trickle sieve tray (dual-flow tray) has two limits. There has to be a minimum limiting velocity of the ascending gas, in order that a certain liquid layer is held on the trickle sieve tray, in order to enable separation-active working of the trickle sieve tray. The upper limit in the velocity of the ascending gas is fixed by the flood point, when the gas velocity leads to backup of the liquid on the trickle sieve tray and prevents it from trickling through.

The longest dimension of the passage orifices of an industrial dual-flow tray (=longest direct line connecting two points on the outline of the passage orifice cross section) is typically 10 to 80 mm (cf., for example, DE 10156988 A1). Normally, the passage orifices are identical within a trickle sieve tray (in other words, they all have the same geometric shape and the same cross section (the same cross-sectional area)). Appropriately in application terms, the cross-sectional areas are circles. In other words, preferred passage orifices of trickle sieve trays are circular holes. The relative arrangement of the passage orifices of a trickle sieve tray advantageously follows a strict triangular pitch (cf., for example, DE 10230219 A1). It is of course also possible for the passage orifices to be configured differently within one and the same trickle sieve tray (to vary over the trickle sieve tray).

Advantageously in application terms, a sequence of trickle sieve trays comprises trickle sieve trays of the same design (identical trickle sieve trays) in a separating column, preferably arranged equidistantly one above another.

According to DE 10156988 A1, it is also possible to employ sequences of trickle sieve trays in separating columns having a uniform (preferably circular) cross section within a dual-flow tray, but varying within the sequence (for example decreasing from the bottom upward).

In general, each dual-flow tray in a corresponding tray sequence concludes flush with the wall of the separating column. However, there are also embodiments in which an intermediate space interrupted only partly by bridges exists between the column wall and tray. Aside from the actual passage orifices, a trickle sieve tray typically has, at most, orifices which serve to secure the tray on support rings or the like (cf., for example, DE 10159823 A1).

Within the normal working range of a sequence of trickle sieve trays, the liquid descending within the separating column trickles downward in droplets from dual-flow tray to dual-flow tray, meaning that the gas phase ascending between the dual-flow trays is permeated by a divided liquid phase. Some of the droplets that hit the lower trickle sieve tray in each case are atomized. The gas stream flowing through the passage orifices bubbles through the liquid layer formed on the surface of the tray, with intense heat and mass transfer between the liquid and the gas.

According to the gas and liquid load, there is a tendency in trickle sieve trays, in the case of column diameters of >2 m, for slightly unequal distributions of liquids to build up, and thus for the liquid hold-up of a tray to vary over a large area or for a circulating wave to form, which can firstly adversely affect the mechanical stability of the column body and secondly reduces the separating action, since the liquid distribution under these conditions is then time-dependent and highly location-dependent. To avoid such non-steady states, it has therefore been found to be advantageous to distribute baffles in the form of vertical metal sheets over the tray cross section, which prevent or at least greatly reduce buildup of liquid within the column body. The height of the metal sheets should correspond approximately to the height of the liquid froth layer that forms. This is typically about 20 cm at customary loads.

The cross section of a separating column is generally circular. This applies correspondingly to the accompanying mass transfer trays.

Dual-flow trays usable for the purposes of this document are described, for example, in Technische Fortschrittsberichte [Technical Progress Reports], vol. 61, Grundlagen der Dimensionierung von Kolonnenböden [Fundamentals of the Dimensioning of Column Trays], pages 198 to 211, Verlag Theodor Steinkopf, Dresden (1967) and in DE 10230219 A1.

The above-described sequence of trickle sieve trays which comprises mass transfer trays without forced flow of the liquid descending onto the tray on the tray is distinguished from sequences of mass transfer trays with such forced liquid flow.

It is a characteristic feature of these mass transfer trays that they additionally have, as well as the passage orifices already described, at least one downcomer. This is at least one downflow orifice present in the mass transfer tray, toward which the liquid which has descended onto the mass transfer tray (for example over an outlet weir (in the simplest embodiment, this may be an upward extension of the downflow orifice with a neck (a chimney; in the case of a circular downflow orifice, a tube))) flows, and which runs into a shaft which feeds the mass transfer tray below in the sequence and which is generally configured with central symmetry with respect to an axis pointing in the longitudinal direction of the column. The cross section of the shaft may vary (for example narrow) along this axis or else be constant.

By virtue of the at least one downcomer of the mass transfer tray, within a sequence of such mass transfer trays, the liquid descending from a higher mass transfer tray can descend independently of the gas or vapor which continues to rise through the passage orifices of this mass transfer tray as at least one feed of liquid to the next lowest mass transfer tray of the sequence.

The essential basis for this separation of the flow paths of descending liquid and ascending gas is the hydraulic seal (the liquid seal or else shaft seal) of the respective downcomer for the ascending gas (a downcomer must not form a bypass past the passage orifices for the ascending gas; the gas stream (the vapor stream) must not ascend past the passage orifices through a downcomer).

Such a hydraulic seal can be achieved, for example, by drawing the downcomer downward (allowing it to run downward) to such an extent that it is immersed deeply enough into the liquid layer on the next lowest mass transfer tray of the sequence (such a seal is also referred to in this document as "static seal"). The liquid level needed for this purpose can be achieved on the lower mass transfer tray, for example, through the height of appropriate outlet weirs.

However, such a design has the disadvantage that the area of the lower mass transfer tray directly below the outflow cross section of a downcomer of the mass transfer tray above (called the feed area) cannot have any passage orifices for the ascending gas and so is not available for heat and mass transfer between the liquid layer formed on the lower mass transfer tray and the ascending gas.

In an alternative embodiment, the lower outflow end of the downcomer is truncated to such an extent that it is no longer immersed into the liquid layer present on the mass transfer tray below. In this case, between the lower end of the at least one downcomer and the mass transfer tray onto which the downcomer runs, a sufficiently large intermediate space remains, in which a froth layer forms and heat and mass transfer can take place between a liquid layer which accumulates (on the lower mass transfer tray) and a gas ascending (through this tray). In other words, in this case, the "feed area" of the at least one downcomer on the mass transfer tray below may also have passage orifices and can thus increase the available exchange area of the mass transfer tray, and hence the separating action thereof.

A static liquid seal of the downcomer can be brought about in this case, for example, with the aid of a collecting cup mounted below the outflow end of the downcomer. Appropriately in application terms, in this case, the outer wall of the collecting cup is truncated to such an extent that the outflow end of the downcomer is immersed into the collecting cup (it is also possible to allow the lower edge of the downcomer to end at the upper edge of the collecting cup). In the course of operation of the column, the liquid flowing downward through the downcomer collects in the collecting cup until it flows over the upper edge of the outer wall of the collecting cup. The lower edge of the downcomer is immersed into the liquid present in the collecting cup, and the collecting cup forms a siphon-like liquid seal of the downcomer.

Alternatively, a truncated downcomer can also be sealed dynamically. For this purpose, the downcomer can be sealed, for example, at the lower end thereof with a tray provided with exit orifices of such dimensions that the liquid is backed up in the downcomer and prevents the penetration of gas (cf., for example, EP 0882481 A1 and DE 10257915 A1). The shaft seal is established in this case dynamically through the pressure drop which arises at the exit orifices. In other words, in the case of static sealing, the downcomer is sealed by virtue of the outflow end thereof being immersed into backed-up liquid, and, in the case of dynamic sealing, construction features at the outflow end of the downcomer have the effect that the exiting liquid suffers a pressure drop which brings about backup of the liquid descending in the downcomer, which causes the seal. In the simplest case, such a pressure drop can be caused by virtue of a small cross section of the exit orifice of the downcomer being selected compared to the mean cross section of the shaft.

For separation-active operation of a sequence of such mass transfer trays, the design of the at least one downcomer is relevant. Firstly, the cross section of the at least one downcomer selected must be sufficiently large (in general, the corresponding cross-sectional area is greater than the cross-sectional area of a passage orifice), in order that the liquid, even at maximum loading of the separating column, can still descend reliably through the at least one downcomer therewith, and does not back up on the tray above. On the other hand, it has to be ensured that, even in the case of minimal liquid loading, the hydraulic seal of the at least one downcomer still exists.

At a low gas loading, there is likewise the risk of liquid trickling through the passage orifices. In addition, the liquid has to be able to back up in a downcomer to such an extent that the weight of the backed-up liquid column is sufficient to convey the liquid into the gas space below the mass transfer tray to which the downcomer is connected. This backup height determines the required minimum length of the downcomer and thus partly determines the tray separation required in a sequence of corresponding mass transfer trays. A significant partial determining factor for the above backup height (backup length) is the pressure drop $\Delta P$ of a mass transfer tray. This pressure drop is suffered by the ascending gas as it flows through the passage orifices, and the "hydrostatic" head of the froth layer on the mass transfer tray. It is responsible for the fact that the pressure in the gas phase of a sequence of such mass transfer trays increases from the top downward. For the "hydrostatic" pressure $h_p$ of the liquid backed up in the downcomer of a mass transfer tray, it is therefore necessary for at least the condition $h_p > \Delta P$ of the mass transfer tray to be met. These connections are also known to the person skilled in the art, for example, from EP 1704906 A1, as is the possibility of ensuring that, with an inflow weir on the lower mass transfer tray, in the case of static sealing of the downcomer of the upper mass transfer tray in the liquid layer on the lower mass transfer tray, the shaft seal still exists even in the case of low loading with descending liquid. However, the use of an inflow weir increases the backup height required in the downcomer to force the liquid backed up therein onto the lower mass transfer tray. Overall, the element of the downcomer enables a broadening of the separation-active working range compared to the trickle sieve tray. A favorable outflow velocity of the liquid backed up in the downcomer from the downcomer in the process according to the invention is, for example, 1.2 m/s.

In addition, it enables forced circulation of the liquid descending onto a mass transfer tray on this tray.

If, for example, only half of a (preferably circular) mass transfer tray has at least one downcomer (which means that all downflow orifices are present with their full extent within the corresponding circle segment), and, in a sequence of at least two identical mass transfer trays of this kind, the mass transfer trays in a separating column are arranged one on top of another such that two mass transfer trays in the separating column, one of which follows the other in the downward direction, are each mounted offset (turned) by 180° relative to one another about the longitudinal axis of the column, such that the downcomers thereof are on opposite sides (in opposite halves) of the separating column, the liquid which descends from an upper mass transfer tray through the at least one downcomer thereof to the mass transfer tray mounted below must necessarily (i.e. of necessity) flow on this lower mass transfer tray, viewed over the lower mass transfer tray, from the at least one feed area of the at least one downcomer of the upper mass transfer tray (that mounted above) (from the at least one feed through the at least one downcomer of the upper mass transfer tray) to the at least one downcomer of this lower mass transfer tray. In other words, the liquid descending from the upper to the lower tray is inevitably conducted across the tray from the at least one feed to the at least one outlet.

Such a liquid flow on a mass transfer tray within a sequence of identical mass transfer trays shall be referred to in this document as a crossflow, the sequence of such identical mass transfer trays as a sequence of identical crossflow mass transfer trays, and the individual mass transfer trays within the sequence as crossflow mass transfer trays.

In the simplest case, the crossflow mass transfer tray is a crossflow sieve tray. Apart from the at least one downcomer, it has passage orifices for the gas ascending in a separating column, and useful embodiments for the configuration thereof are in principle all of those addressed for the trickle sieve tray. A crossflow sieve tray preferably likewise has circular holes as passage orifices, and these likewise, advantageously for application purposes, have a uniform radius. As already mentioned, the at least one downcomer enables the liquid descending in a separating column, in a sequence of crossflow sieve trays, irrespective of the flow path of the vapor ascending in the sequence, to descend (through the passage orifices) from a higher crossflow sieve tray to the next lowest crossflow sieve tray. On the lower tray, the liquid flows in crosscurrent from the at least one feed of the lower tray, which is formed by the at least one outlet of the higher crossflow sieve tray, to the at least one downcomer (to the at least one outlet) of the lower tray, the desired liquid height on the lower crossflow sieve tray being partly ensured, for example, by the height of at least one outlet weir over which the liquid can flow to the at least one downcomer. In addition, the liquid is retained on the crossflow sieve tray by the backup pressure of the vapor ascending in the separating column. If the vapor loading of a crossflow sieve tray, however, falls below a minimum value, the result may be trickling of the liquid through the passage orifices, which reduces the separating action of the crossflow sieve tray and/or leads to the crossflow sieve tray running dry.

This risk of running dry can be counteracted by providing the downflow orifice of the at least one downcomer with an outlet weir and extending the respective passage orifice in the upward direction with a neck (a chimney; in the case of a circular passage orifice, a tube).

Normally mounted over the end of the neck are vapor-deflecting hoods (bubble caps, inverted cups) (these may in the simplest case be placed on with screw connections to the neck (for example at the front and back) and are effectively pulled over the neck), which are immersed into the liquid backed up on the tray. The vapor ascending through the respective passage orifice at first flows through the neck thereof into the accompanying hood, in which it is deflected, in order then, in contrast to the crossflow sieve tray, to flow in parallel to the tray surface from the hood into the liquid backed up thereon (such a "parallel outflow" is generally favorable in processes according to the invention in that it is able to "blow away" undesirably formed polymer particles and thus to bring about a self-cleaning effect). The gas streams (vapor streams) exiting from adjacent hoods, preferably distributed equidistantly over the trays, agitate the liquid backed up on the tray and form a froth layer therein, in which the heat and mass transfer takes place. Such crossflow mass transfer trays are also referred to as crossflow bubble-cap trays or crossflow hood trays. Since they have backed-up liquid even in the case of low loading with ascending gas (vapor) and thus are at no risk of running dry, they are also referred to as hydraulically sealed crossflow trays. Compared to crossflow sieve trays, they typically require higher capital costs and cause higher pressure drops of the gas ascending through them. The passage orifice of these trays designed (configured) as described is also referred to as bubble-cap passage orifice or hood passage orifice, in contrast to the simple sieve passage orifice of a sieve tray.

The most important component of the crossflow bubble-cap tray is the bubble cap (cf., for example, DE 10243625 A1 and Chemie-Ing.-Techn. Volume 45, 1973/No. 9+10, p. 617 to 620). According to the configuration and arrangement of the bubble caps (vapor deflecting hoods, hoods), crossflow bubble-cap trays are divided, for example, into crossflow round bubble-cap trays (the cross sections of passage orifice, chimney (neck) and bubble cap (vapor deflecting hood) are round (for example the cylinder bubble-cap tray or the flat bubble-cap tray), tunnel crossflow trays (the cross sections of passage orifice, chimney and bubble cap (hood) are rectangular; the passages with their bubble caps are arranged one after another within rows arranged alongside one another, with the longer rectangular edge aligned parallel to the crossflow direction of the liquid) and crossflow Thormann® trays (the cross sections of passage orifice, chimney and bubble cap (hood) are rectangular; the passages with their bubble caps are arranged one after another within rows arranged alongside one another, with the longer rectangular edge aligned at right angles to the crossflow direction of the liquid). Crossflow Thormann trays are described, for example, in DE 19924532 A1 and in DE 10243625 A1, and the prior art acknowledged in these two documents.

Figure 3:
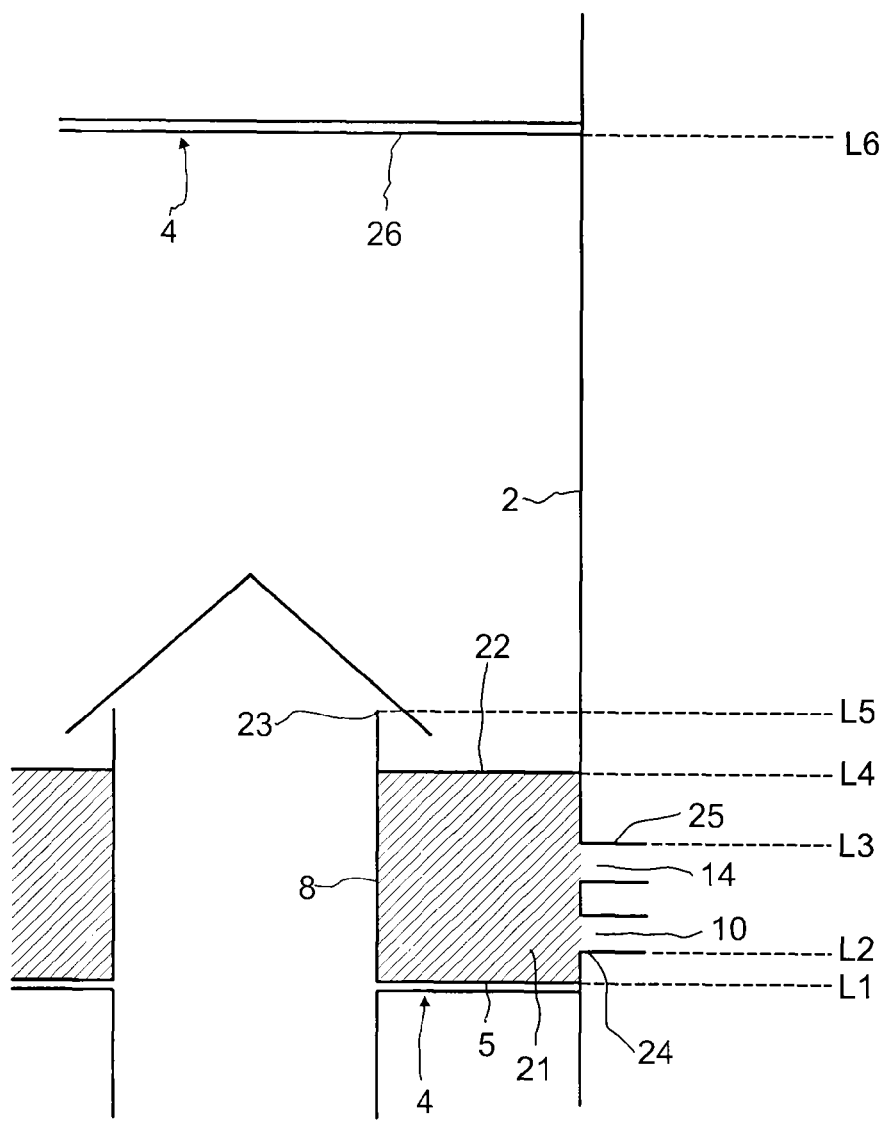

The bubble-cap edge in crossflow bubble-cap trays may have very different forms (cf. DE 10243625 A1 and Chemie-Ing. Techn. Volume 45, 1973/No. 9+10, p. 617 to 620). FIG. 3 from Chemie-Ing. Techn. Volume 45, 1973/No. 9+10, p. 618 shows some examples of the serrated and slotted edge. The serrations and slots are typically shaped such that the vapor emerging from the bubble cap into the liquid backed up on the mass transfer tray dissolves very easily into a large number of bubbles or vapor jets. The above FIG. 3 and various figures in DE 10243625 A1 also show illustrative embodiments of bubble-cap edges having a sawtooth-like structure, the teeth of which are additionally equipped with guide fins (guide surfaces) ("slots bent open"). The guide fins are intended to impose a tangential exit direction on the gas stream (vapor stream) exiting from the sawtooth-like slots bent open (direct the gas exit into the liquid in an oblique direction), as a result of which the surrounding liquid receives a directed movement pulse which, in cooperation with the arrangement of the bubble caps (vapor deflecting hoods), can lead to a directed liquid flow on the crossflow bubble-cap tray, which is superimposed on the crossflow which is established, viewed over the mass transfer tray (frequently, such slots bent open are also referred to as forcing slots). For example, in a sequence of crossflow Thormann trays, the liquid on a lower crossflow Thormann tray does not flow directly across the tray, but rather, in the manner described above, is driven in a meandering manner from the at least one feed to the at least one outlet. The space between two hoods of a crossflow Thormann tray arranged one after the other in crossflow direction forms a channel in each case, in which the liquid flows. The detailed configuration of a crossflow Thormann tray is additionally normally in such a manner that the liquid flows in countercurrent in two channels which are successive in each case in crossflow direction (cf., for example, FIG. 3 of DE 10243625 A1). The meandering crossflow which results in this manner prolongs the flow path of the liquid from the at least one feed to the at least one outlet, which promotes the separating action of a crossflow Thormann tray.

As already stated, in a crossflow bubble-cap tray, the gas emerging from the bubble cap, in contrast to the crossflow sieve tray, is introduced parallel to the tray surface into the liquid backed up on the crossflow bubble cap tray. Frictional and buoyancy forces ensure that, with increasing distance of the emerging gas stream from the bubble-cap edge, more and more substreams thereof are deflected in a direction at right angles to the crossflow bubble-cap tray and ultimately escape from the liquid layer. With increasing gas loading of a bubble cap, the velocity of the gas stream emerging from it grows, which increases the distance from the edge of the bubble cap ("the effective range of the bubble cap") up to which the above-described deflection occurs.

This dependence of the effective range of a rigid bubble cap on the gas loading can be counteracted by configuring (designing) the passage orifice of a crossflow mass transfer tray as a valve (as a valve passage orifice). The resulting crossflow mass transfer trays are referred to as crossflow valve trays (cf., for example, DD 279822 A1, DD 216633 A1 and DE 102010001228 A1).

The term "crossflow valve trays" in this document thus covers crossflow mass transfer trays which have passage orifices (tray holes) with limited-stroke plate, ballast or lifting valves (floating flaps) which adjust the size of the vapor passage orifice to the respective column loading.

In a simple configuration, the passage orifices of the tray are covered for the aforementioned purpose with covers or plates (disks) movable in the upward direction. In the course of passage of the ascending gas, the lids (plates, disks) are raised by the gas stream in a corresponding guide structure (guide cage) additionally mounted over the respective passage orifice (which is normally firmly anchored on the tray) and finally reach a stroke height corresponding to the gas loading (instead of a guide cage, the disk may also possess upwardly movable valve legs anchored to the tray, the upward mobility of which has an upper limit). The gas stream ascending through the passage orifice is deflected at the underside of the raised lid (plate, disk) in a similar manner to that in the bubble cap (in the case of a bubble-cap passage orifice) and exits from the exit region formed under the raised plate (lid, disk) and, as is the case for the bubble-cap tray, enters the liquid backed up on the tray parallel thereto. The plate stroke thus controls the size of the gas exit region and automatically adjusts to the column loading until the upper end of the guide cage limits the maximum possible stroke height. The plates may have spacers directed downward, such that, at low gas loading, the valve closes only to such an extent that the space provided by the spacers still permits vigorous mixing of the horizontal gas outflow with the crossflowing liquid. Spacers also counteract sticking of the valve disk on the tray. Through suitable configuration of the valve elements of a crossflow valve tray, the blowing direction of the valve element can be adjusted, and hence the forced liquid flow on the crossflow valve tray can additionally be influenced (cf., for example, DD 216 633 A1). The principle of crossflow valve trays, and valve trays usable for the purposes of the present document, can be found, for example, in Technische Fortschrittsberichte, volume 61, Grundlagen der Dimensionierung von Kolonnenböden, pages 96 to 138. As well as the above-described moving valves, the person skilled in the art is also aware of fixed valves. These are normally disk-shaped, or trapezoidal, or rectangular units which are punched out of the tray plate and are connected thereto via fixed legs directed upward.

Especially in the case of relatively large diameters of a separating column, on crossflow mass transfer trays, a notable liquid gradient naturally forms proceeding from the at least one feed until attainment of the outlet weir of the at least one outlet (the gradient of the backup height of the liquid feeds the crossflow (to a limited degree)). The result of this is that, in regions with a relatively low liquid height, due to the resulting lower resistances, the ascending vapor (the ascending gas) can pass through the liquid layer more easily in comparative terms. This can ultimately give rise to an inhomogeneous gas loading of the crossflow mass transfer tray (there is preferential flow through the regions with a lower liquid height (a lower flow resistance)), which impairs the separating action thereof. A compensating effect is possible in this respect through the use of, for example, bubble caps of adjustable height (alternatively, the bubble-cap size can also be altered) in the case of crossflow bubble-cap trays, or by use of, for example, plates (lids) with different weight in the case of crossflow valve trays, such that the mass transfer tray produces gas essentially homogeneously over its cross section (where the liquid height on the crossflow mass transfer tray is lower, the height of the bubble cap is, appropriately in application terms, selected at a correspondingly lower level, or the weight of the stroke plate (stroke lid) is selected at a correspondingly higher level; the height of the bubble cap can, for example, also be lowered by controlled shortening of the length of the corresponding chimney, at the end of which the bubble cap is optionally screwed on; alternatively or additionally, for example, the serration/slot structure of the bubble-cap edge can also be varied in order to bring about the desired flow resistance compensation; ideally, the adjustment is made over the crossflow mass transfer tray such that, in operation of the separating column, every bubble cap present on a crossflow bubble-cap tray causes the same flow resistance for the ascending gas). Otherwise, the passages (the passage orifices) of a crossflow mass transfer tray are generally advantageously configured uniformly.

Orifices running (from the top downward) through a crossflow mass transfer tray, the cross-sectional area of which is typically more than 200 times smaller than the overall cross-sectional area of all other orifices of the crossflow mass transfer tray (not including the cross section of the at least one downcomer), do not constitute (separating) passage orifices for the gas ascending through the crossflow mass transfer tray and are therefore not counted as part thereof. For example, such orifices may be tiny emptying holes through which hydraulically sealed crossflow trays can empty when a separating column is shut down. It is also possible for such orifices to serve for screw connection purposes.

Sequences of mass transfer trays having at least one downcomer, in which the at least one feed and the at least one outlet are present, for example, in the same half of the (circular) mass transfer tray, or in which the at least one feed is in the middle of the tray and the at least one outlet is at the edge of the tray, do not constitute a sequence of crossflow mass transfer trays in the sense of the application (of the invention).

The efficacy of crossflow mass transfer trays designed as described is typically less than that of one theoretical plate (one theoretical separation stage). A theoretical plate (or theoretical separation stage) shall be understood in this document quite generally to mean that spatial unit of a separating column which comprises separating internals and is used for a thermal separation process which brings about enrichment of a substance in accordance with the thermodynamic equilibrium. In other words, the term "theoretical plate" is applicable both to separating columns with mass transfer trays and to separating columns with structured packings and/or random packings.

The prior art recommends the use of sequences of at least two identical crossflow mass transfer trays, in separating columns including those comprising separating internals, which are employed for performance of thermal separation processes between at least one gas stream ascending in the separating column and at least one liquid stream descending in the separating column, and wherein at least one of the streams comprises at least one (meth)acrylic monomer. For example, documents DE 19924532 A1, DE 10243625 A1 and WO 2008/090190 A1 recommend the additional use of a sequence of identical hydraulically sealed crossflow mass transfer trays in a separating column for performance of a process for fractional condensation of a product gas mixture comprising acrylic acid from a heterogeneously catalyzed gas phase partial oxidation of $C_3$ precursors of acrylic acid with molecular oxygen, which comprises, from the bottom upward, at first dual-flow trays and subsequently hydraulically sealed crossflow mass transfer trays.

Figure 4:
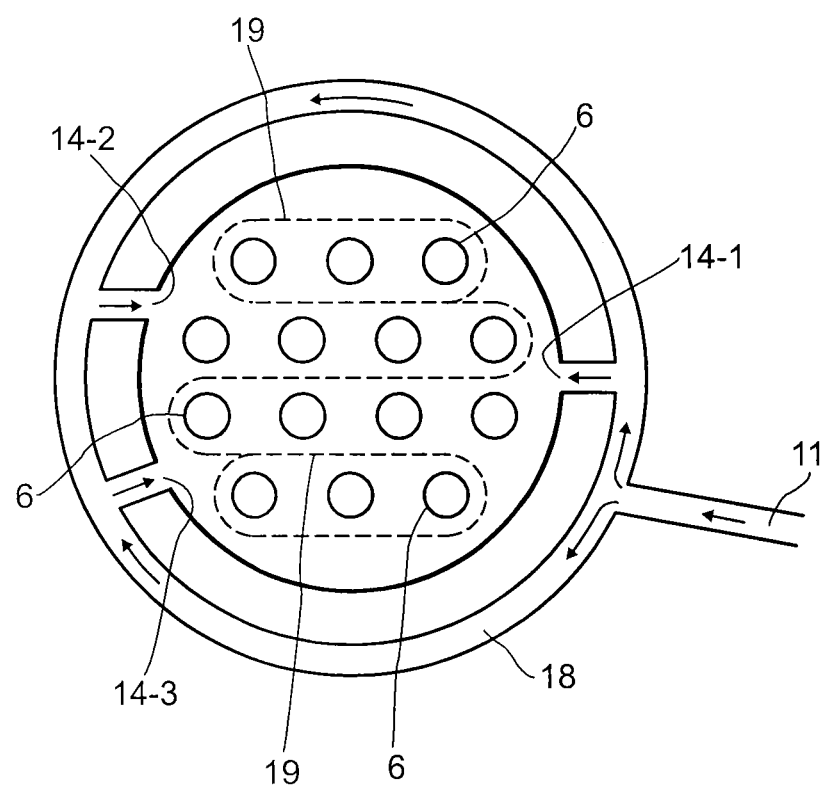

A characteristic feature of the sequences of crossflow mass transfer trays recommended in the prior art is that the lower of two successive crossflow mass transfer trays in the sequence in each case, in the direction of crossflow from the at least one feed thereof to the at least one downcomer thereof, has passage orifices only in the region between the at least one feed and the at least one downcomer (the at least one downflow orifice) (cf., for example, FIGS. 3 and 4 of DE 10243625 A1, FIG. 1 of DD 279822 A1, FIG. 1 of DD 216633 A1, and FIG. 1 from Chemie-Ing.-Techn. Volume 45, 1973/No. 9+10, pages 617 to 620).

A problematic property of (meth)acrylic monomers is the tendency thereof to unwanted polymerization, which cannot completely be suppressed even by the addition of polymerization inhibitors, particularly in the liquid phase.

A disadvantage of known separating columns is that, in the case of continuous performance of the thermal separation process, there is comparatively frequently formation of unwanted polymer over prolonged periods of operation in the mass transfer trays. This is particularly disadvantageous because the operator of the thermal separation process, due to the unwanted polymer formation, has to interrupt the thermal separation process time and again in order to remove the polymer formed. This is because the latter can partly or completely block the passage orifices of the mass transfer tray. Moreover, the free-radical polymerization of (meth)acrylic monomers is normally markedly exothermic, i.e. has high evolution of heat. There is the risk of polymerization proceeding so violently that the separating column comprising the polymerization mixture explodes.

It is therefore an object of the present invention to provide a column and a thermal separating process of the types specified at the outset, in which polymerization of the material present within the separating column can be prevented or at least reduced.

According to the invention, this object is achieved by a column having the features of claim 1 and a thermal separating process having the features of claim 18. Advantageous configurations and developments are apparent from the dependent claims.

Accordingly, the invention relates to a column for thermal treatment of a fluid, having a cylindrical, vertical column body which forms a column cavity, and a mass transfer tray which is arranged in the column cavity and forms a collecting area. The inventive column further comprises a circulation device having at least one drain orifice formed in the column body above the collecting area, a circulation line in fluid connection with the drain orifice and at least one recycling orifice which is in fluid connection with the circulation line and is formed in the column body above the collecting area.

The spatial terms "top", "bottom", "horizontal" and "vertical" relate, unless explicitly stated otherwise, to the orientation of the column during operation.

It has been found that the unwanted polymer forms, especially in the so-called dead zones of the mass transfer tray. In such dead zones, the residence time of the fluid in the mass transfer tray is particularly long. Such a long residence time promotes polymerization. The circulation device envisaged in the inventive column can generate liquid circulation on the collecting area of the mass transfer tray, which prevents the formation of dead zones. The liquid stream entrains any fluid residues. The residence time of liquid on the collecting area of the mass transfer tray is reduced as a result. More particularly, the residence time distribution becomes narrower, meaning that there is less volume of liquid that resides on the mass transfer tray for a prolonged period. This can advantageously prevent the polymer from partially or completely occluding passage orifices of the mass transfer tray. Moreover, the explosion risk caused by the polymerization mixture is reduced.

In one configuration of the inventive column, the drain orifice is disposed immediately above the lowermost region of the collecting area of the mass transfer tray. The lower edge of the drain orifice may especially be arranged at the same height as the lowermost region of the collecting area, such that the liquid present in the collecting area can run essentially completely to the drain orifice without leaving residues on the collecting area. Advantageously, this effectively prevents polymer formation when a fluid having a tendency to polymerization is treated in the column.

In one configuration of the column of the invention, a plurality of mass transfer trays are arranged with vertical spacing in the column cavity and the drain orifice and the recycling orifice are arranged vertically between two adjacent mass transfer trays with vertical spacing. In this case, more particularly, the ratio of the vertical separation of the lowest region of the collecting area of the mass transfer tray from the lower edge of the drain orifice to the vertical separation of the lowest region of the collecting area of the mass transfer tray from the underside of the mass transfer tray disposed directly above is within a range from 0 to 0.3, especially within a range from 0 to 0.1.

The recycling orifice in the inventive column may either open into the column cavity above the drain orifice, or the recycling orifice opens into the column cavity at the same height as the drain orifice. Advantageously, the arrangement of the recycling orifice relative to the drain orifice is chosen such that a liquid circulation is produced on the collecting area of the mass transfer tray, and this reaches all areas of the mass transfer tray, such that, more particularly, no dead zones form.

In one configuration of the column of the invention, the ratio of the vertical separation of the lowest region of the collecting area of the mass transfer tray from the upper edge of the recycling orifice to the vertical separation of the lowest region of the collecting area of the mass transfer tray from the underside of the mass transfer tray disposed directly above is within a range from 0 to 0.3, especially within a range from 0 to 0.2. These geometric ratios advantageously assure introduction of the liquid typically beneath the liquid level in the collecting area. The recycling orifice too is especially disposed immediately above the lowest region of the collecting area of the mass transfer tray. In this way, it is advantageously possible to achieve particularly good mixing of the liquid in the collecting area of the mass transfer tray.

In a development of the inventive column, a nozzle for producing a liquid jet on entry of the liquid into the column cavity is disposed in the recycling orifice. If a plurality of recycling orifices are disposed in the column, it is especially possible for each of these recycling orifices to have such a nozzle. By means of the nozzle(s), it is possible to even more effectively prevent the formation of dead zones in which polymer forms in the course of treatment of a corresponding fluid.

The circulation line and the recycling orifice(s) are especially arranged such that the recycled liquid enters the column cavity radially. This advantageously even more effectively prevents the formation of dead zones.

In a development of the inventive column, a plurality of spaced-apart recycling orifices are formed in the column body. These recycling orifices are each in fluid connection with the circulation line. In this way, liquid removed via the drain orifice can be fed back to the column cavity above the mass transfer tray at a plurality of points. This advantageously even more effectively achieves no formation of dead zones in the collecting tray.

In one configuration of the inventive column, the mass transfer tray, or at least one tray in the column, has passage orifices for the gas ascending from the bottom. In these passage orifices, cylindrical bodies extend upward. The cylindrical bodies are especially provided with hoods, caps or roofs at a certain distance, such that gas can leave the cylindrical bodies in a lateral direction, without the possibility of movement of the liquid trickling down from the mass transfer tray above in countercurrent to the gas. These vertical bodies on the mass transfer tray, also referred to as chimneys, may in special cases, as well as a circular cross section, also have a square, rectangular, elliptical cross-sectional area. The distance (A) of the hoods, caps or roofs from the cylindrical body having diameter (D) is generally A<2D. This type of tray is a chimney tray which collects at least some of the liquid that trickles down from the upper tray in the space between the chimneys, from which it can be sent to a specific other use.

In one configuration of the column of the invention, the upper edges of the cylindrical body are overflow edges. The ratio of the vertical separation of the lowest region of the collecting area of the mass transfer tray from the lower edge of the drain orifice to the vertical separation of the lowest region of the collecting area of the mass transfer tray from the height of the lowermost overflow edge of the cylindrical bodies is, for example, within a range from 0 to 0.1, especially within a range from 0 to 0.05. In addition, in one configuration of the column of the invention, the ratio of the vertical separation of the lowest region of the collecting area of the mass transfer tray from the upper edge of the recycling orifice to the vertical separation of the lowest region of the collecting area of the mass transfer tray from the height of the lowermost overflow edge of the cylindrical bodies is within a range from 0 to 0.9, especially within a range from 0 to 0.3. These geometric ratios advantageously assure introduction of the liquid typically beneath the liquid level in the collecting area. In this way, it is advantageously possible to achieve particularly good mixing of the liquid in the regions between the cylindrical bodies.

In an inventive configuration of this tray, the recycling orifices are arranged relative to the cylindrical bodies so as to result in a meandering liquid flow on the collecting area of the mass transfer tray. In this way, the liquid flow can especially reach all the regions of the collecting area on the mass transfer trays, such that no dead zones form on the collecting tray in spite of the interruptions by the cylindrical bodies.

In a development of the inventive column, the circulation line has an opening for supply of a further liquid. Through this opening, it is especially possible to supply an inert liquid or a liquid comprising polymerization inhibitors.

More particularly disposed in the circulation line is a pump which can be used to pump away liquid that collects on the collecting area of the mass transfer tray and feed it back to the column cavity through the recycling orifice. By means of the pump or an additional regulating valve, the liquid stream on the mass transfer tray can be controlled or regulated. The pump or the regulating valve can also be coupled to a sensor which measures the liquid level on the collecting area of the mass transfer tray. Depending on this liquid level, the pump can then regulate the circulation and/or liquid removal of the liquid.

The inventive column can especially be used as a separating column. The separating column has a sequence of mass transfer trays. Mass transfer trays used are especially the trays mentioned at the outset, i.e. mass transfer trays without forced flow, such as trickle sieve trays and dual-flow trays, and mass transfer trays with forced liquid flow, for example crossflow mass transfer trays, especially crossflow bubble-cap trays, or crossflow hood trays, crossflow Thormann trays and crossflow valve trays.

The clear distance between two immediately successive trays within the inventive column is especially not more than 700 mm, preferably not more than 600 mm or not more than 500 mm. Appropriately in application terms, the clear distance within the tray sequence is 300 to 500 nm. In general, the tray separation should not be less than 250 mm.

The height of the column body is, for example, greater than 5 m, especially greater than 10 m. However, it is also possible for the height of the column body to exceed 30 m or 40 m.

Further separating internals may be disposed between the trays. The separating internals improve the mass separation in the separating column. These further internals may be provided, for example, in the form of packings, especially structured or ordered packings, and/or beds of random packings. Among the random packings, preference is given to those comprising rings, helices, saddles, Raschig, Intos or Pall rings, Berl or Intalox saddles, Top-Pak etc. Structured packings particularly suitable for extraction columns for use in accordance with the invention are, for example, structured packings from Julius Montz GmbH in D-40705 Hilden, for example the Montz-Pak B1-350 structured packing. Preference is given to using perforated structured packings made from stainless steel sheets. Packed columns having ordered packings are known per se to those skilled in the art and are described, for example, in Chem.-Ing. Tech. 58 (1986) no. 1, pages 19-31 and in the Technische Rundschau Sulzer 2/1979, pages 49 ff. from Gebrüder Sulzer Aktiengesellschaft in Winterthur, Switzerland.

The invention further relates to a thermal separating process between at least one gas ascending within a column, as described above, and at least one liquid descending within the column.

In one configuration of the process of the invention, the liquid introduced via the recycling orifice is introduced below the liquid level in the collecting area.

In the process of the invention, the ascending gas and/or the descending liquid especially comprises (meth)acrylic monomers.

The thermal separating process according to the invention may, for example, be a process for fractional condensation for separation of acrylic acid from a product gas mixture comprising acrylic acid from a heterogeneously catalyzed gas phase oxidation of a $C_3$ precursor compound (especially propene and/or propane) of the acrylic acid with molecular oxygen to give acrylic acid.

The separating column (condensation column) may be configured as described in documents DE 10243625 A1 and WO 2008/090190 A1, except that, in the case of the trays used therein, at least some of the above-described circulation devices are provided.

In the process according to the invention, the tendency to polymerization is particularly great because of the use of (meth)acrylic monomers. Such unwanted polymerization is prevented in the process according to the invention by virtue of liquid that collects on the collecting area of a mass transfer tray being pumped away through the drain orifice and being fed back to the column cavity through the recycling orifice(s).

There follows an elucidation of working examples of the inventive column and working examples of the process according to the invention with reference to the drawings.

Figure 2:
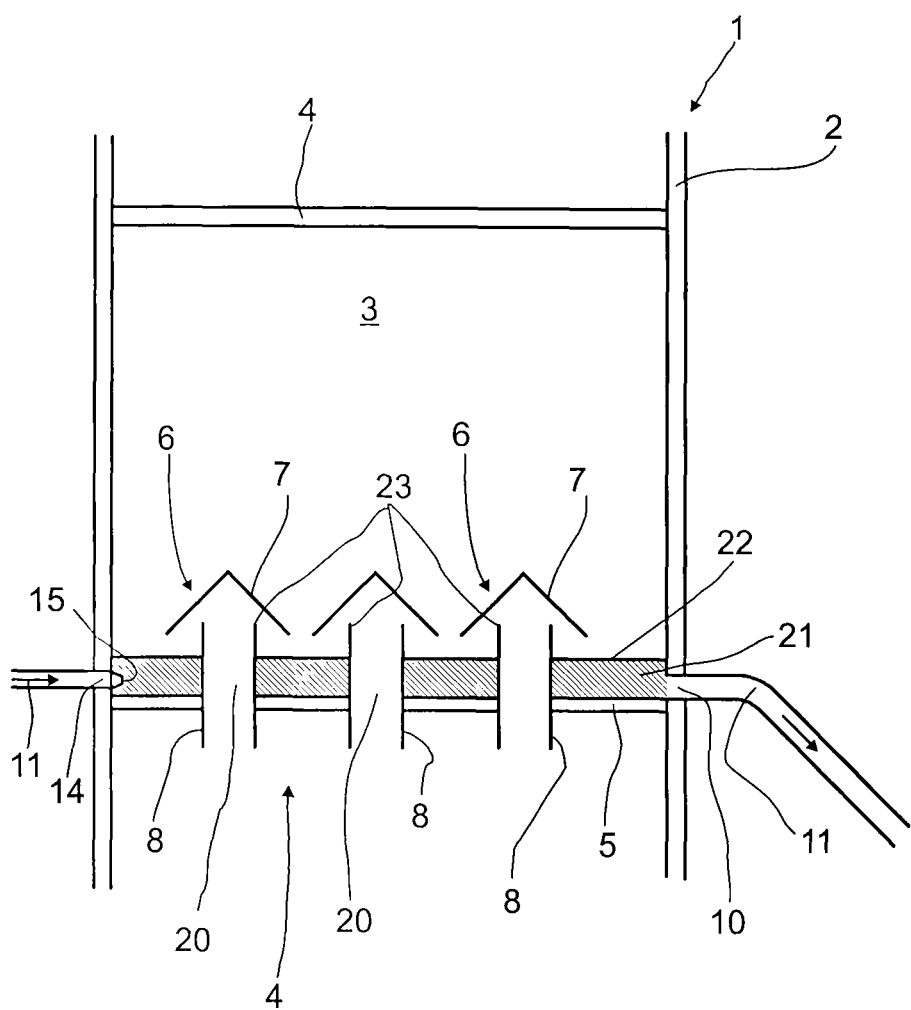

FIG. 1 shows a schematic vertical section of part of a column in a working example of the invention, FIG. 2 shows a schematic vertical section of part of a column in a further working example of the invention, FIG. 3 illustrates the vertical arrangement of devices in the column of the further working example and FIG. 4 shows a cross section of the column of yet another working example of the invention.

The working example described hereinafter relates to a separating column 1 as used, for example, in a process for fractional condensation for separation of acrylic acid from a product gas mixture comprising acrylic acid from a heterogeneously catalyzed gas phase partial oxidation of a $C_3$ precursor compound (especially propene and/or propane) of the acrylic acid with molecular oxygen to give acrylic acid.

FIG. 1 shows the separating column 1 known per se in schematic form. It comprises a cylindrical column body 2, the axis of which is aligned vertically. The column body 2 is essentially a hollow cylinder. This means that the shell 7 of the column body 2 forms a column cavity 3. The column body 2 is manufactured from stainless steel. On the outside, the separating column 1 is normally thermally insulated in a conventional manner. The height of the separating column 1 is 40 m.

Several mass transfer trays 4 are secured in the column cavity 3, are horizontal and are mounted with vertical spacing. The mass transfer trays 4 serve as separating internals which improve separation in the separating column 1. The partial view shown in FIG. 1 shows one of the mass transfer trays 4.

The mass transfer tray 4 in this case is a chimney tray. This mass transfer tray 4 comprises a plate which is secured horizontally in the column body 2 and forms, on the upper face, the collecting area 5. Passage orifices 20 are formed in the plate. Chimneys 6 are inserted into these passage orifices 20. In this case, fluid-tight cylindrical bodies 8, also referred to as chimney bodies, are inserted into the passage orifices 20. Liquid 21 can collect on the collecting area 5 up to the upper edge 23 of the cylindrical bodies 8. The orifice formed within each cylindrical body 8 is covered by a covering hood 7, meaning that the orifice is screened off from liquid dripping downward. Chimney trays of this kind are known per se.

In the inventive column 1, a circulation device 9 is provided. This circulation device 9 comprises a drain orifice 10 formed immediately above the collecting area 5 in the shell of the column body 2. The drain orifice 10 is connected to a circulation line 11. Through the drain orifice 10, liquid 21 which collects on the collecting area 5 is conducted out of the column cavity 3.

Disposed in the circulation line 11 is a pump 12 which conveys the liquid conducted out through the circulation line 11 to a recycling orifice 14. The recycling orifice 14 is disposed above the upper edge of the cylindrical bodies 8 of the chimneys 6. The circulation line 11 opens into this recycling orifice 14, with a nozzle 15 disposed in the recycling orifice 14 or at the end of the circulation line 11. Through the nozzle 15, the liquid is sprayed back onto the mass transfer trays 4 above the drain orifice 10. The circulation line 11 and the recycling orifice 14 are arranged such that the recycled liquid enters the column cavity 3 radially. The nozzle 15 is formed such that a liquid flow is produced in all regions on the collecting area 5 of the mass transfer tray 4, and this prevents long residence times of liquid volumes from arising on the collecting area.

In a further working example shown in FIG. 2, the recycling orifice 14 is arranged at the same height as the drain orifice 10 or at least below the upper edge 23 of the cylindrical bodies 8 of the chimneys 6. The recycling orifice 14 in this case is optionally arranged beneath the liquid level 22 on the collecting area 5. In this case, what is called a motive jet nozzle 15 is disposed in the recycling orifice 14, and this is used to inject the liquid into the standing liquid 21, which produces a liquid flow on the collecting area 5.

The further devices that form part of the circulation unit 9 are not shown in FIG. 2 for reasons of clarity. They are the same as already described above with reference to FIG. 1.

FIG. 3 illustrates possible vertical arrangements of the collecting area 5, the drain orifice 10, the recycling orifice 14, the liquid level 22, the upper edges 23 of the cylindrical bodies 8 and the underside 26 of the mass transfer tray 4 disposed directly above. The collecting area 5 is disposed at the height L1, the lower edge 24 of the drain orifice 10 at the height L2, and the upper edge 25 of the recycling orifice 14 at the height L3. The liquid level 22 is disposed at the height L4. The cylindrical bodies 8 in the chimneys 6 form overflow edges at their upper edges 23. The lowermost overflow edge of the cylindrical bodies 8 is disposed at the height L5. The underside 26 of the mass transfer tray 4 disposed directly above the collecting area 5 is disposed at the height L6.

In the case of the working example of FIG. 3, the recycling orifice 14 and the drain orifice 10 are disposed between the two adjacent mass transfer trays 4 and beneath the liquid level 22. In addition, the ratio of the vertical separation of the collecting area 5 of the mass transfer tray 4 from the lower edge 24 of the drain orifice 10 to the vertical separation of the collecting area 5 of the mass transfer tray 4 from the height L5 of the lowermost overflow edge of cylindrical bodies 8 is within a range from 0 to 0.1, meaning that:

$$0 \le \frac{\text{abs}(L1 - L2)}{\text{abs}(L1 - L5)} \le 0.1$$

In addition, the ratio of the vertical separation of the collecting area 5 of the mass transfer tray 4 from the upper edge 25 of the recycling orifice 14 to the vertical separation of the collecting area 5 of the mass transfer tray 4 from the height L5 of the lowermost overflow edge of the cylindrical bodies 8 is within a range from 0 to 0.9, meaning that:

$$0 \le \frac{\text{abs}(L1 - L3)}{\text{abs}(L1 - L5)} \le 0.9$$

If the collecting tray 4 is not a chimney tray but a collecting tray 4 which has a different configuration and does not have a cylindrical body 8, the ratio of the vertical separation of the collecting area 5 of the mass transfer tray 4 from the lower edge 24 of the drain orifice 10 to the vertical separation of the collecting area 5 of the mass transfer tray 4 from the underside 26 of the mass transfer tray 4 disposed directly above is within a range from 0 to 0.3, meaning that:

$$0 \le \frac{\text{abs}(L1 - L2)}{\text{abs}(L1 - L5)} \le 0.3$$

In addition, the ratio of the vertical separation of the collecting area 5 of the mass transfer tray 4 from the upper edge 25 of the recycling orifice 14 to the vertical separation of the collecting area 5 of the mass transfer tray 4 from the underside 26 of the mass transfer tray 4 disposed directly above is within a range from 0 to 0.3, meaning that:

$$0 \le \frac{\text{abs}(L1 - L3)}{\text{abs}(L1 - L5)} \le 0.3$$

In further working examples, it is also possible to select other configurations of the collecting area of the mass transfer tray 4 relative to the drain orifice 10. For example, a channel formed in the mass transfer trays 4 may open into the drain orifice 10. In addition, the circulation line 11 may open into a plurality of recycling orifices 14.

The circulation line 11 additionally has an opening 13. In this opening 13, a feed line 16 for a further liquid opens into the circulation line 11. The feed line 16 has a valve 17 through which the liquid feed into the circulation line 11 can be controlled or regulated.

FIG. 4 shows a cross section at the level of the recycling orifice 14 of the inventive column 1. FIG. 4 shows yet another working example in which not just one recycling orifice 14 is formed in the column body 2, but several recycling orifices 14-1, 14-2 and 14-3. These recycling orifices 14-1 to 14-3 are connected via a ring line 18 to the circulation line 11. The recycling orifices 14-1 to 14-3 in this case are arranged relative to the chimneys 6 so as to result in a meandering liquid flow 19 on the collecting area 5 of the mass transfer tray 4. The recycling orifices 14-1, 14-2 and 14-3 and the drain orifice (10) may be arranged here from a vertical point of view as elucidated above with reference to FIG. 3.

It is pointed out that it is also possible to use other mass transfer trays among those mentioned by way of introduction in all the working examples.

There follows a description of a working example of the process according to the invention which is executed with the above-described separating column 1 of one of the working examples.

The process is a thermal separating process between at least one gas ascending in the separating column 1 and at least one liquid descending in the separating column 1. The ascending gas and/or the descending liquid especially comprises (meth)acrylic monomers.

In the separation process, a fractional condensation for separation of acrylic acid from a product gas mixture comprising acrylic acid from a heterogeneously catalyzed gas phase partial oxidation of a $C_3$ precursor compound (especially propene and/or propene) of the acrylic acid with molecular oxygen to give acrylic acid is conducted in a separating column 1 comprising separating internals. The separating column 1 comprises, from the bottom upward, a plurality of mass transfer trays 4. For example, there are disposed first dual-flow trays and then crossflow capped trays or chimney trays, with a circulation device 9 formed in at least some thereof, as described above. Otherwise, the process is conducted as described in documents DE 19924532 A1, DE 10243625 A1 and WO 2008/090190 A1. In this case, however, liquid is pumped away continuously from the collecting areas 5 of the mass transfer trays 4 by means of the circulation devices 9 and fed back to the collecting areas 5 in the respective mass transfer trays 4 via the recycling orifice 14 or the recycling orifices 14-1 to 14-3.

The term "$C_3$ precursor" of acrylic acid encompasses those chemical compounds which are obtainable in a formal sense by reduction of acrylic acid. Known $C_3$ precursors of acrylic acid are, for example, propane, propene and acrolein. However, compounds such as glycerol, propionaldehyde, propionic acid or 3-hydroxypropionic acid should also be counted among these $C_3$ precursors. Proceeding from these, the heterogeneously catalyzed gas phase partial oxidation with molecular oxygen is at least partly an oxidative dehydrogenation. In the relevant heterogeneously catalyzed gas phase partial oxidations, the $C_3$ precursors of acrylic acid mentioned, generally diluted with inert gases, for example molecular nitrogen, CO, $CO_2$, inert hydrocarbons and/or water vapor, are passed in a mixture with molecular oxygen at elevated temperatures and optionally elevated pressure over transition metal mixed oxide catalysts, and converted oxidatively to a product gas mixture comprising acrylic acid.

Typically, the product gas mixture comprising acrylic acid from a heterogeneously catalyzed gas phase partial oxidation of $C_3$ precursors (e.g. propene) of acrylic acid with molecular oxygen over catalysts in the solid state, based on the total amount of the specified constituents present (therein), has the following contents:

1% to 30% by weight of acrylic acid,
0.05% to 10% by weight of molecular oxygen,
1% to 30% by weight of water,
0% to 5% by weight of acetic acid,
0% to 3% by weight of propionic acid,
0% to 1% by weight of maleic acid and/or maleic anhydride,
0% to 2% by weight of acrolein,
0% to 1% by weight of formaldehyde,
0% to 1% by weight of furfural,
0% to 0.5% by weight of benzaldehyde,
0% to 1% by weight of propene, and as the remainder, inert gases, for example nitrogen, carbon monoxide, carbon dioxide, methane and/or propane.

The partial gas phase oxidation itself can be performed as described in the prior art. Proceeding from propene, the partial gas phase oxidation can be performed, for example, in two successive oxidation stages, as described, for example, in EP 700 714 A1 and in EP 700 893 A1. It will be appreciated, however, that it is also possible to employ the gas phase partial oxidations cited in DE 19740253 A1 and in DE 19740252 A1.

In general, the temperature of the product gas mixture leaving the partial gas phase oxidation is 150 to 350° C., frequently 200 to 300° C.

Direct cooling and/or indirect cooling cools the hot product gas mixture appropriately at first to a temperature of 100 to 180° C., before it is conducted, for the purpose of fractional condensation, into region C (the bottom) of separating column 1. The operating pressure which exists in the separation column 1 is generally 0.5 to 5 bar, frequently 0.5 to 3 bar and in many cases 1 to 2 bar.

The invention claimed is:

1. A column for thermal treatment of a fluid, the column comprising:
   a cylindrical, vertical column body which forms a column cavity;
   a mass transfer tray which is disposed in the column cavity and forms a collecting area;
   a circulation device having, at east one drain orifice formed in the column body above the collecting area;
   a circulation line in fluid connection with the drain orifice; and
   at least one recycling orifice which is in fluid connection with the circulation line and is formed in the column body above the collecting area,
   wherein:
   a plurality of mass transfer trays are arranged with vertical spacing in the column cavity, and the drain orifice and the recycling orifice are arranged vertically between two adjacent mass transfer trays with vertical spacing; and
   the ratio of the vertical separation of the lowest region of the collecting area of the mass transfer tray from the lower edge of the drain orifice to the vertical separation of the lowest region of the collecting area of the mass transfer tray from the underside of the mass transfer tray disposed directly above is within a range from 0 to 0.3.

2. The column according to claim 1, wherein the recycling orifice opens into the column cavity above the drain orifice.

3. The column according to claim 1, wherein a nozzle for producing a liquid jet on entry of the liquid into the column cavity is disposed in the recycling orifice.

4. The column according to claim 1, wherein the circulation line and the recycling orifice are arranged such that the liquid recycled enters the column cavity radially.

5. The column according to claim 1, wherein a plurality of spaced-apart recycling orifices are formed in the column body, each of which is in fluid connection with the circulation line.

6. The column according to claim 1, wherein the mass transfer tray has passage orifices for gas ascending from the bottom, and cylindrical bodies extend upward in the passage orifices.

7. The column according to claim 6, wherein the recycling orifices are arranged relative to the cylindrical bodies so as to result in a meandering liquid flow on the collecting area of the mass transfer tray.

8. The column according to claim 6, wherein the mass transfer tray is a chimney tray and the cylindrical body is a chimney body.

9. The column according to claim 1, wherein the circulation line has an opening for supply of a further liquid.

10. The column according to claim 1, wherein a pump arranged in the circulation line pumps away liquid that collects on the collecting area of the mass transfer tray and feeds it back to the column cavity through the recycling orifice.

11. A thermal separation process, comprising thermally separating at least one gas ascending within the column of claim 1 and at least one liquid descending within the column.

12. The process according to claim 11, wherein liquid is introduced via the recycling orifice below the liquid level in the collecting area.

13. The process according to claim 11, wherein the ascending gas, the descending liquid, or both, comprises at least one (meth)acrylic monomer.

14. The column according to claim 1, wherein the drain orifice is disposed immediately above the lowermost region of the collecting area of the mass transfer tray.

15. A column for thermal treatment of a fluid, the column comprising:
   a cylindrical, vertical column body which forms a column cavity;
   a mass transfer tray which is disposed in the column cavity and forms a collecting area;
   a circulation device having at least one drain orifice formed in the column body above the collecting area;
   a circulation line in fluid connection with the drain orifice; and
   at least one recycling orifice which is in fluid connection with the circulation line and is formed in the column body above the collecting area,
   wherein the recycling orifice opens into the column cavity at the same height as the drain orifice.

16. A column for thermal treatment of a fluid, the column comprising:
   a cylindrical, vertical column body which forms a column cavity;
   a mass transfer tray which is disposed in the column cavity and forms a collecting area;
   a circulation device having, at least one drain orifice formed in the column body above the collecting area;
   a circulation line in fluid connection with the drain orifice;
   at least one recycling orifice which is in fluid connection with the circulation line and is formed in the column body above the collecting area,
   wherein:
   a plurality of mass transfer trays are arranged with vertical spacing in the column cavity, and the drain orifice and the recycling orifice are arranged vertically between two adjacent mass transfer trays with vertical spacing; and
   the ratio of the vertical separation of the lowest region of the collecting area of the mass transfer tray from the upper edge of the recycling orifice to the vertical separation of the lowest region of the collecting area of the mass transfer tray from the underside of the mass transfer tray disposed directly above is within a range from 0 to 0.3.

17. A column for thermal treatment of a fluid the column comprising:
   a cylindrical, vertical column body which forms a column cavity;

a mass transfer tray which is disposed in the column cavity and forms a collecting area;
a circulation device having at least one drain orifice formed in the column body above the collecting area;
a circulation line in fluid connection with the drain orifice; and
at least one recycling orifice Which is in fluid connection with the circulation line and is formed in the column body above the collecting area, wherein:

the mass transfer tray has passage orifices for gas ascending from the bottom, and cylindrical bodies extend upward in the passage orifices; and the upper edges of the cylindrical body are overflow edges and the ratio of the vertical separation of the lowest region of the collecting area of the mass transfer tray from the lower edge of the drain orifice to the vertical separation of the lowest region of the collecting area of the mass transfer tray from the height of the lowermost overflow edge of the cylindrical bodies is within a range from 0 to 0.1.

18. A column for thermal treatment of a fluid, the column comprising:

a cylindrical, vertical column body which forms a column cavity;
a mass transfer tray which is disposed in the column cavity and forms a collecting area;
a circulation device having at least one drain orifice formed in the column body above the collecting area;
a circulation line in fluid connection with the drain orifice; and
at least one recycling orifice which is in fluid connection with the circulation line and is formed in the column body above the collecting area, wherein:

the mass transfer tray has passage orifices for gas ascending from the bottom, and cylindrical bodies extend upward in the passage orifices; and the upper edges of the cylindrical body are overflow edges and the ratio of the vertical separation of the lowest region of the collecting area of the mass transfer tray from the upper edge of the recycling orifice to the vertical separation of the lowest region of the collecting area of the mass transfer tray from the height of the lowermost overflow edge of the cylindrical bodies is within a range from 0 to 0.9.

* * * * *